United States Patent
Matsumoto et al.

[11] Patent Number: 5,777,103
[45] Date of Patent: Jul. 7, 1998

[54] PROCESS FOR PRODUCING CYCLOHEXYLAZETIDINONE

[75] Inventors: Takaji Matsumoto; Toshiyuki Murayama; Shigeru Mitsuhashi; Takashi Miura, all of Kanagawa, Japan

[73] Assignee: Takasago International Corporation, Tokyo, Japan

[21] Appl. No.: 808,270

[22] Filed: Feb. 28, 1997

[30] Foreign Application Priority Data

Dec. 12, 1996 [JP] Japan ................. 8-332021

[51] Int. Cl.$^6$ .................. C07F 205/08; C07B 49/00
[52] U.S. Cl. ................................. 540/200
[58] Field of Search ........................... 540/200

[56] References Cited

U.S. PATENT DOCUMENTS 5,393,751  2/1995  Serdai .................. 540/302

*Primary Examiner*—Mark L. Berch
*Attorney, Agent, or Firm*—Sughrue, Mion, Zinn, Macpeak & Seas, PLLC

[57] ABSTRACT

A process for producing cyclohexylazetidinone expressed by the formula(IV) comprises condensing the magnesium enolate compound expressed by the formula (II) with acyloxyazetidinone expressed by the formula (III), wherein Me is a methyl group; $R^1$ is a hydroxyl-protecting group, $R^2$ is an acyl group, and X is a halogen atom.

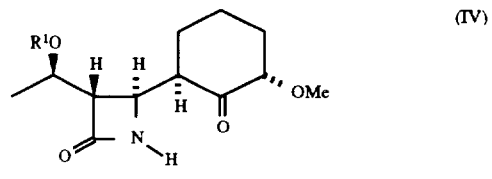

(IV)

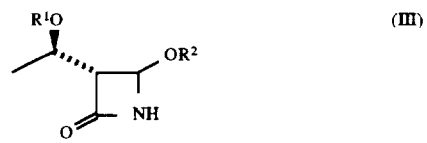

(III)

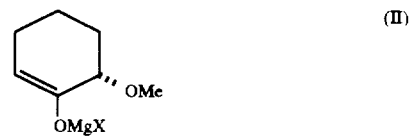

(II)

6 Claims, No Drawings

PROCESS FOR PRODUCING CYCLOHEXYLAZETIDINONE

BACKGROUND OF THE INVENTION

1. Field of the Invention

The present invention relates to a novel and industrially applicable process for producing a cyclohexylazetidinone derivative which is useful as an intermediate for the synthesis of tricyclic β-lactam antibiotics (trinem antibiotics).

2. Description of the Related Art

Tricyclic β-lactam compounds (trinem) are known to have excellent antibacterial activities (EP 0416953 A2), and a typical example of them is Sanfetrinem expressed by the following formula (VI).

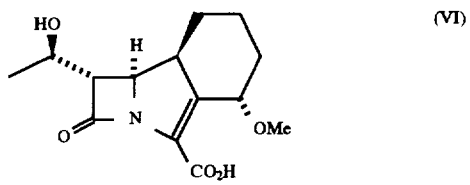

(VI)

For the synthesis of this compound, a compound expressed by the following formula (IV), in which $R^1$ is a trialkylsilyl group, is a key intermediate.

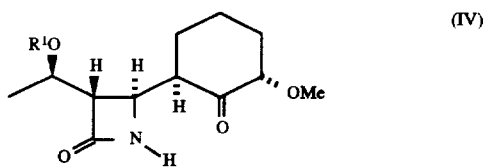

(IV)

With respect to the synthesis of such an intermediate, for example, the following methods have been proposed.

Perboni, A., et al. (EP 0466509 A1) disclosed a process in which acetoxyazetidinone (IIIa) is coupled with 1-trimethylsilyloxycyclohexene in the presence of a Lewis acid catalyst to prepare cyclohexanone, and subsequently, reduction to cyclohexene, stereoselective epoxidation, methanolysis, and, oxidation are performed, as shown in the following scheme.

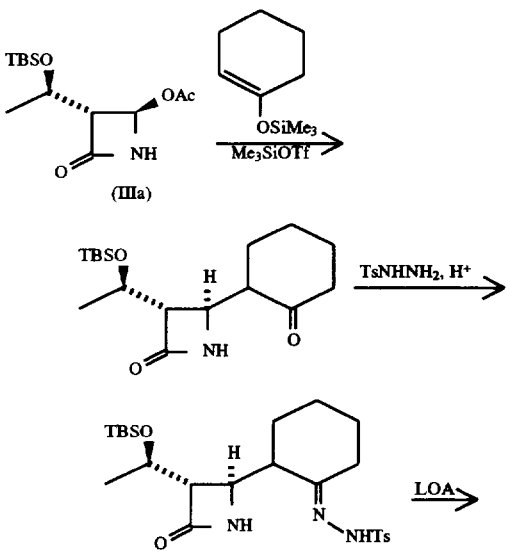

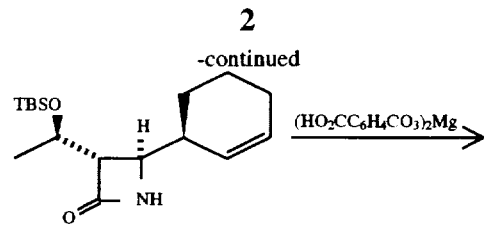

As to introducing cyclohexene to acetoxyazetidinone (IIIa) S. Biondi, et al. (EP 617017 A1) and T. Rossi, et al. [J. Am. Chem. Soc., 117, 9604 (1995)] reported methods using allylborane in the presence of a Lewis acid, as shown in the following scheme.

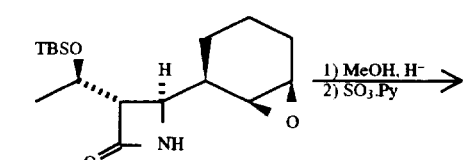

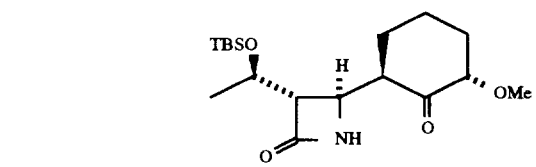

Further, T. Rossi et al. (WO 95/26333) disclosed a method for direct condensation of azetidinone(IIIa) with (2S)-2-methoxycyclohexanone using stannic chloride, as shown in the following scheme.

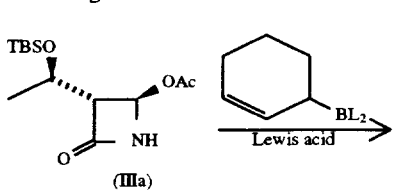

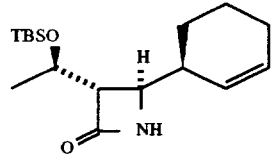

Additionally, A. Pecunioso et al. (GB 2287709 A) also disclosed a method using stannic chloride for coupling with silyl enol ether, as shown in the following scheme.

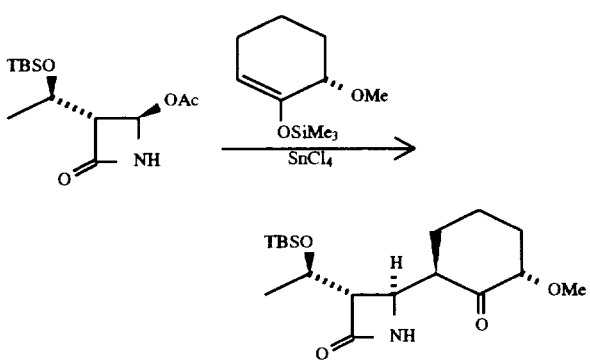

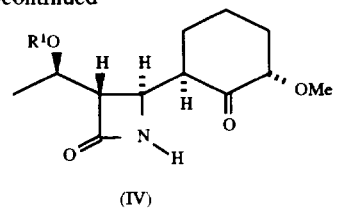

The above-mentioned methods, however, have some drawbacks. For example, the method of Perboni, A. et al. has a relatively large number of reaction steps, and therefore, the yield is lowered. In the methods using a Lewis acid as disclosed by S. Biondi et al., T. Rossi et al., T. Rossi, and A. Pecunioso, large amounts of a Lewis acid are used, which requires a great deal of load in post-treatment, especially in disposal of waste fluid.

SUMMARY OF THE INVENTION

Under such circumstances, the inventors earnestly investigated an industrial process for synthesizing cyclohexylazetidinone (IV) and have accomplished a novel process as described below.

Accordingly, the object of the present invention is to provide a process for producing cyclohexylazetidinone (IV). Specifically, the process of the present invention comprises treating (2S)-2-methoxycyclohexanone expressed by the formula (I) with a base to prepare a magnesium enolate compound expressed by the formula (II), and condensing the magnesium enolate compound with (3R,4R)-4-acyloxy-3-[(1R)-1-hydroxyethyl]-azetidine-2-one expressed by the formula (III), in which $R^2$ is an acyl group, to stereoselectively produce the objective cyclohexyazetidinone (IV), as shown in the following scheme

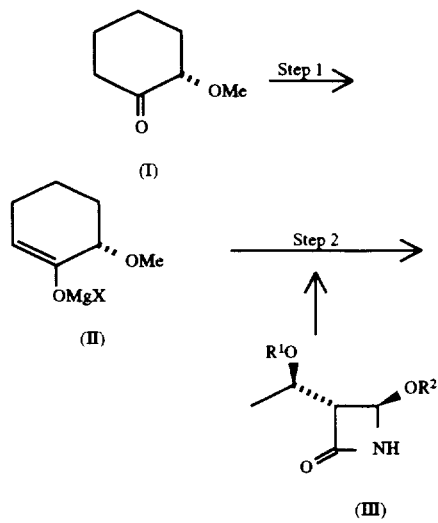

wherein Me is a methyl group, $R^1$ is a hydroxyl-protecting group, for example a tert-butyldimethylsilyl group, trimethylsilyl group, $R^2$ is an acyl group, and X is a halogen atom. The acyl group includes an alkanoyl group having from 1 to 9 carbon atoms, a cycloalkanoyl group having from 4 to 7 carbon atoms or benzoyl group. The alkanoyl group includes formyl group, acetyl group, propionyl group, butanoyl group, pentanoyl group, hexanoyl group, heptanoyl group or octanoyl group. The cycloalkanoyl group includes a cyclopropylcarbonyl group, cyclobutylcarbonyl group, cyclopentylcarbonyl group or cyclohexylcarbonyl group.

The base to be used in the present invention is a magnesium amide expressed by the general formula (V).

$R^3R^4NMgX$         (V)

which is prepared from a secondary amine expressed by the general formula (VII),

$R^3R^4NH$         (VII)

wherein each of $R^3$ and $R^4$ is a lower alkyl group, a lower alkenyl group, a substituted or non-substituted aralkyl group, or a substituted or non-substituted phenyl group, and $R^3$ and $R^4$ may be identical or different, by reacting with a Grignard reagent expressed by the general formula (VIII), $R^5MgX$         (VIII)

wherein $R^5$ is a lower alkyl group, a lower alkenyl group, a substituted or non-substituted aralkyl group, or a substituted or non-substituted phenyl group, and X is a halogen atom.

According to the present invention, the condensation reaction between (2S)-2-methoxycyclohexanone and acyloxyazetidinone for producing tricyclic β-lactam intermediates can be achieved through preparation of a magnesium enolate compound of (2S)-2-methoxycyclohexanone. The process of the present invention is free from a Lewis acid and disposal of a harmful waste fluid, and therefore, the objective cyclohexylazetidinone derivatives can be produced in an industrially advantageous and simple manner.

DESCRIPTION OF THE PREFERRED EMBODIMENT

As to the secondary amine to be used in the abovementioned reaction, the following amine compounds can be listed as examples: diethylamine, diisopropylamine, dipropylamine, dibutylamine, diisobutylamine, di-tertiary-butylamine, dicyclohexylamine, diphenylamine, dibenzylamine, dicyclopentylamine, dihexylamine, methylethylamine, ethylpropylamine, ethylisopropylamine, morpholine, piperidine, pyrrolidine, indole, and 1,1,1,3,3,3-hexamethyldisilazane. Preferable examples are diethylamine and diisopropylamine, and the most preferable example is diisopropylamine. The amount of the secondary amine to be used should be 1 to 2 molar equivalent, and preferably, 1.1 to 1.3 molar equivalent relative to that of the Grignard reagent.

As to the Grignard reagent, the following compounds can be listed as examples: methylmagnesium chloride, methylmagnesium bromide, methylmagnesium iodide, ethylmagnesium chloride, ethylmagnesium bromide, ethylmagnesium iodide, propylmagnesium chloride, propylmagnesium bromide, propylmagnesium iodide, isopropylmagnesium chloride, isopropylmagnesium bromide, isopropylmagnesium iodide, butylmagnesium chloride, butylmagnesium bromide, butylmagnesium iodide, isobutylmagnesium chloride, isobutylmagnesium bromide, isobutylmagnesium iodide, tert-butylmagnesium chloride, tert-butylmagnesium bromide, tert-butylmagnesium iodide, phenylmagnesium chloride, phenylmagnesium bromide, phenylmagnesium iodide, benzylmagnesium chloride, benzylmagnesium bromide, benzylmagnesium iodide, vinylmagnesium chloride, allylmagnesium chloride, and allylmagnesium bromide. Preferable examples of the Grignard reagent are ethylmagnesium bromide, isopropylmagnesium bromide, and tert-butylmagnesium chloride, and the most preferable example is tert-butylmagnesium chloride. The amount of the Grignard reagent to be used is 1 to 1.5 molar equivalent, and preferably, 1.05 to 1.2 molar equivalent, relative to that of methoxycyclohexanone.

Practically, magnesium amide is prepared by adding the Grignard reagent to the secondary amine, or by the inverse procedure thereof. The reaction temperature for the preparation is –30° C. to 100° C., and preferably, 0° C. to 20° C. The reaction time should be a few minutes to 24 hours, and preferably, 30 minutes to 1 hour. Any solvents which do not affect the reaction can be used as the solvent for the preparation of the magnesium amide, and each may be used solely or together with other solvents as a mixture solvent. Specifically, such a solvent may be selected from hydrocarbons such as hexane, heptane, octane, nonane, decane, benzene, toluene, and xylene; halogenated hydrocarbons such as dichloromethane, chloroform, and 1,2-dichloroethane; ethers such as tetrahydrofuran, dioxane, dimethoxyethane, diisopropyl ether, diethylene glycol dimethyl ether; and acetonitrile. Preferably, the solvent should be selected from ethers such as tetrahydrofuran, dioxane, dimethoxyethane, diisopropyl ether, diethylene glycol dimethyl ether, and most preferably, tetrahydrofuran.

Next, a magnesium enolate compound is prepared by adding (2S)-methoxycyclohexanone to the above-prepared magnesium amide. The reaction temperature for the preparation is –30° C. to 50° C., and preferably, 0° C. to 10° C. The reaction time should be a few minutes to 24 hours, and preferably, 10 minutes to 3 hours. Any solvents which do not affect the reaction can be used as the solvent for the preparation of magnesium amide, and each may be used solely or together with other solvents as a mixture solvent. Specifically, such a solvent may be selected from hydrocarbons such as hexane, heptane, octane, nonane, decane, benzene, toluene, and xylene; halogenated hydrocarbons such as dichloromethane, chloroform, and 1,2-dichloroethane; ethers such as tetrahydrofuran, dioxane, dimethoxyethane, diisopropyl ether, diethylene glycol dimethyl ether; and acetonitrile. Preferably, the solvent should be selected from ethers such as tetrahydrofuran, dioxane, dimethoxyethane, diisopropyl ether, diethylene glycol dimethyl ether, and most preferably, tetrahydrofuran. Though not being especially limited, the amount of the solvent to be used is normally 2-fold to 50-fold by weight, and preferably 5-fold to 10-fold by weight, of that of (2S)-2-methoxycyclohexanone. The production of the magnesium enolate compound by this process can be confirmed by silyl enol etherification using trimethylchlorosilane.

Alternatively, the magnesium enolate compound can also be prepared, for example, by the following method (1), (2), or (3).

(1) Treating an a-halocarbonium compound with metallic magnesium (reacting a corresponding 2-halogenocyclohexanone derivative with metallic magnesium), as shown in the scheme below (P. Fellmann, et al., Tetrahedron, 1978, 1349);

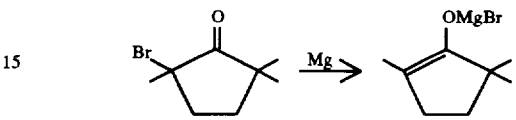

(2) Preparing a lithium enolate compound from lithium diisopropylamide or the like, and exchanging the metal with halogenated magnesium (reacting a corresponding lithium enolate derivative with magnesium halide), as shown in the scheme below (G. Stork, et al., J. Am. Chem. Soc., 1968, 4464); and

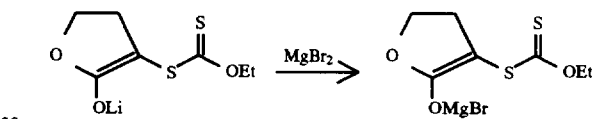

(3) Reacting silyl enol ether with a Grignard reagent (S. Matsui, et al., Bull. Chem. Soc. Jpn., 1987, 1853), as shown in the scheme below (reacting a corresponding O-trialkylsilyl enol ether derivative with an alkyl magnesium halide).

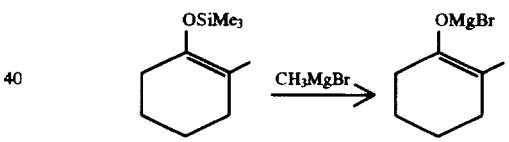

According to method (2), for example, (2S)-2-methoxycyclohexanone is reacted with lithium diisopropylamide to obtain a lithium enolate compound, and the lithium enolate compound is reacted with magnesium bromide to prepare the objective magnesium enolate compound. Meanwhile, according to method (3), the objective magnesium enolate compound can be prepared, for example, by reacting 1-trimethylsilyloxy-6-(S)-methoxy-1-cyclohexene, which can be synthesized from (2S)-2-methoxycyclohexanone, with methylmagnesium bromide.

As described above, the method and conditions for preparing the magnesium enolate compound are not especially limited, and they may be selected from the viewpoint of labor saving, cost saving, or the like.

Next, as to the condensation reaction between the magnesium enolate compound (II) and acyloxyazetidinone (III), the reaction can be performed after the preparation of the magnesium enolate compound (II).

When the generated secondary amine affects condensation and decreases the yield of the reaction product, it might be better to remove the generated secondary amine from the reaction mixture in which the magnesium enolate compound (II) was prepared before the condensation reaction. The amount of the magnesium enolate compound (II) to be used in the reaction should be 1.0 to 1.5 molar equivalent, and preferably, 1.05 to 1.2 molar equivalent, relative to that of acyloxyazetidinone (III). The solvent to be used in the condensation may be selected from hydrocarbons such as hexane, heptane, octane, nonane, decane, benzene, toluene, and xylene; halogenated hydrocarbons such as dichloromethane, chloroform, and 1,2-dichloroethane; ethers such as tetrahydrofuran, dioxane, dimethoxyethane, diisopropyl ether, diethylene glycol dimethyl ether; esters such as ethyl acetate, propyl acetate, isopropyl acetate, and butyl acetate; N,N-dimethylformamide; dimethylsulfoxide; and acetonitrile. Preferably, the solvent should be selected from hydrocarbons such as benzene, toluene, and xylene; ethers such as tetrahydrofuran, dioxane, dimethoxyethane, diisopropyl ether, and diethylene glycol dimethyl ether; or esters such as ethyl acetate, propyl acetate, isopropyl acetate, and butyl acetate, and more preferably, the solvent should be toluene or butyl acetate. The reaction is normally performed at a temperature of −30° C. to 40° C., and preferably, −10° C. to 20° C. Though not being especially limited, the amount of the solvent to be used is normally 2-fold to 50-fold by weight, and preferably, 5-fold to 10-fold by weight, of that of (2S)-2-methoxycyclohexanone.

According to the present invention, as described above, the condensation reaction between (2S)-2-methoxycyclohexanone and acyloxyazetidinone for producing tricyclic β-lactam intermediates can be achieved through the preparation of a magnesium enolate compound of (2S)-2-methoxycyclohexanone. The process of the present invention is free of a Lewis acid and disposal of a harmful waste fluid, and, therefore, the objective cyclohexylazetidinone derivatives can be produced in an industrially advantageous and simple manner.

The present invention will be illustrated in detail with the examples below which are not presented to limit the scope of the present invention. Incidentally, the following are apparatuses and materials used for measurements performed in the examples below.

Melting point measuring apparatus: MP-500D manufactured by Yanako Institute for Apparatus Development;

$^1$H NMR spectrum measuring apparatus: AM-400 (400 MHz) manufactured by Bruker Corporation, and Gemini-2000 (200 MHz) manufactured by Varian Corporation;

Internal Standard Substance: tetramethylsilane (in CDCl$_3$)

REFERENTIAL EXAMPLE 1

Synthesis of (2S)-2-Methoxycyclohexanone

The starting material (2S)-2-methoxycyclohexanone was synthesized from (1S,2S)-2-methoxycyclohexanol by a known method as disclosed in GB 2287709A or WO 95/26333.

To a 1 liter 4-necked flask, (1S,2S)-2-methoxycyclohexanol (53.57 g,0.411 mol) and methylene chloride (250 ml) were placed, and subsequently, 2,2,6,6-tetramethyl-1-piperidinyloxy free radical(1.28 g, 0.008 mol), potassium bromide (1.47 g, 0.0123 mol), and 8%-sodium hydrogencarbonate solution (52 ml, 0.0494 mol) were added and cooled to 0° C. To this mixture, 3.1N sodium hypochlorite solution (254 ml, 0.787 mol) was added dropwise over a period of 6 hours while maintaining a temperature of 0° C. to 5° C. After the disappearance of the raw material (1S,2S)-2-methoxycyclohexanol was confirmed by gas chromatography, sodium sulfite (5.36 g, 0.0425 mol) was added to the mixture to perform fractionation. Distillation was then performed, and the aqueous phase was subjected to extraction with two 25 ml portions of methylene chloride. The solvent was distilled off under a reduced pressure, and further distillation was performed to obtain (2S)-2-methoxycyclohexanone (51.67 g). The yield was 95%, the boiling point and optical purity of the product were 84° C./24 mmHg and 100%e.e., respectively. Incidentally, the gas chromatography for confirming the disappearance of (1S,2S)-2-methoxycyclohexanol was performed using the following apparatus and conditions.

Apparatus for gas chromatography: HP-5890 series II Plus manufactured by Hewlett Packard Co.;

Column: Neutrabond-1 (0.25 mm–30 m) manufactured by GL Sciences Co., Ltd.;

Carrier gas: Helium

Injection temperature: 220° C.

Detection temperature: 250° C.

Oven temperature: initial 80° C. through final 250° C. with a heating rate of 2° C./min.

Further, the gas chromatography for measuring the optical purity of (2S)-2-methoxycyclohexanone was performed using the following apparatus and conditions.

Apparatus for gas chromatography: GC-14A manufactured by Shimadzu Corporation;

Column: Chiraldex B-TA (0.25 mm–30 m) manufactured by Astec Corporation;

Carrier gas: Helium

Injection temperature: 200° C.

Detection temperature: 250° C.

Oven temperature: 90° C.

EXAMPLE 1

(a) Synthesis of magnesium enolate(II)

To a solution of diisopropylamine(1.96 ml, 14 mmol) in tetrahydrofuran(10 ml) which had been cooled to 0° C., a tetrahydrofuran solution(6.49 ml, 12 mmol) containing 1.85 mol/liter of tert-butylmagnesium chloride was added dropwise and stirred for 30 min. To this mixture, a solution of (2S)-2-methoxycyclohexanone (1.41 g, 11 mmol) in tetrahydrofuran (10 ml) was added dropwise at 0° C. over period of 20 min., the solvent and the amine produced in the reaction mixture were completely distilled off under reduced pressure to give the magnesium enolate(II) as a viscous oil.

The production of magnesium enolate(:I) by this process can be confirmed by silyl enol etherification using trimethylchlorosilane as follows.

To the solution consisting of magnesium enolate (II), which was prepared by the procedure in EXAMPLE 1, and tetrahydrofuran (10 ml) was added dropwise trimethylchlorosilane(1.52 ml, 12 mmol) at 0° C., and the reaction mixture was warmed to room temperature and stirred for 2 h. The reaction was quenched by 0.5N-hydrochloric acid and extracted with hexane. The organic layer was separated and washed with sodium hydrogencarbonate solution and water, and dried over magnesium sulfate. Removal of the solvent gave a colorless oil. The crude product was distilled to give a 1-trimethylsilyloxy-6-(S)-methoxy-1-cyclohexene(1.50 g). The yield was 75%, and the boiling point of the product was 86° C./15 mmHg. $^1$H-NMR(200 MHz, CDCl$_3$); 4.92–4.99(m, 1H), 3.45–3.52 (m, 1H), 3.40 (s, 3H), 1.80–2.10(m, 3H) 1.40–1.52(m, 3H), 0.18(s, 9H)

EXAMPLE 2

Synthesis of (3S,4R)-3-[(R)-1-((tert-butyldimethylsilyl)oxy)ethyl]-4-[(1R,3S)-3-methoxy-2-oxocyclohexyl]azetidin-2-one To the oil of magnesium enolate(II), which was prepared by the procedure described in EXAMPLE 1, butyl acetate (15 ml) was added and cooled to 5° C. Afterwards, a solution of (3R,4R)-4-acetoxy-3-|(1R)-1-tert-butyldimethylsilyloxyethyl|-2-azetidinone (2.87 g, 10 mmol) in butyl acetate (15 ml) was added dropwise at 5° C. over a period of 20 min., and stirred for a further 30 min. Methanol (10 ml) was then added and stirred for 10 min, and subsequently, 2N hydrochloric acid was added for fractionation. The organic phase was washed with a saturated sodium hydrogencarbonate solution and water, and concentrated under a reduced pressure to obtain a crude product of (3S,4R)-3-|(R)-1-((tert-butyldimethylsilyl)oxy)ethyl|-4-|(1R,3S)-3-methoxy-2-oxocyclohexyl|azetidin-2-one. The crude product contained 3.02 g of the objective β-isomer (IV). The yield was 85%, and the β:α ratio was 92:8.

ANALYTICAL EXAMPLE 1

Analysis of Cyclohexylazetidinone Derivative

The diastereoselectivity of the synthesized cyclohexylazetidinone derivative was examined by high performance liquid chromatography under the following conditions. Incidentally, the yield and purity of the synthesized cyclohexylazetidinone derivative were determined using an internal standard.

Detector: L-4000 UV Detector manufactured by Hitachi, Ltd.;

Pump: L-6000 Pump manufactured by Hitachi, Ltd.;

Column: Inertsil ODS-2 (4.6 mm–250 mm) manufactured by GL Sciences Co., Ltd.;

Eluting solution: acetonitrile/water=70/30

Flow rate: 1.0 ml/min.;

Detecting wavelength: 205 nm;

Internal standard: n-Hexyl benzoate manufactured by Tokyo Kasei Kogyo Co., Ltd.

Further, the above obtained crude product of the cyclohexylazetidinone derivative was recrystallized through dissolving in heptane to obtain 2.31 g of a white crystal compound. The physicochemical properties of The crystal compound were as follows, and similar to those reported in WO 95/26333 by T. Rossi, et al.

Melting point: 132° C. to 133° C.; $^1$H NMR (400 MHz, CDCl$_3$) d:5.86(s, 1H), 4.19(m, 1H), 3.99(m, 1H), 3.57(t, 1H), 3.28(s, 3H), 3.09(m, 1H), 2.88(m, 1H) 2.23(m, 1H), 2.10(m, 1H), 1.99(m, 1H), 1.74–1.6(m, 2H), 1.58(m, 1H), 1.25(d, 3H), 0.87(s, 9H), 0.08(s, 3H), 0.06(s, 3H).

EXAMPLE 3

(3S,4R)-3-|(R)-1-((tert-butyldimethylsilyl)oxy)ethyl|-4-|(1R,3S)-3-methoxy-2-oxocyclohexyl|azetidin-2-one was synthesized as a crude product by the same procedure as in Example 2 except that tetrahydrofuran was used as the solvent for the condensation reaction with (3R,4R)-4-acetoxy-3-|(R)-1-((tert-butyldimethylsilyl)oxy)ethyl|-azetidin-2-one. The crude product contained 2.63 g of the objective β-isomer (IV). The yield was 74%, and the β:α ratio was 87:13.

EXAMPLE 4

(3S, 4R)-3-|(R)-1-(tert-butyldimethylsilyl)oxy)ethyl|-4-|(1R,3S)-3-methoxy-2-oxocyclohexyl|azetidin-2-one was synthesized as a crude product by the same procedure as in Example 2 except that diethylamine (1.45 ml, 14 mmol) was used instead of diisopropylamine, and that tetrahydrofuran was used as the solvent for the condensation reaction with (3R,4R)-4-acetoxy-3-|(R)-1-((tert-butyldimethylsilyl)oxy) ethyl|-azetidin-2-one. The crude product contained 2.70 g of the objective β-isomer (IV). The yield was 76%, and the β:α ratio was 86:14.

EXAMPLES 5 THROUGH 10

Similar to the procedures in Examples 2 through 4 above, the objective cyclohexylazetidinone was produced using various secondary amines and solvents, and under various reaction conditions, as shown in Table 1 below. The yields and the β:α a ratios of the obtained products are also shown in Table 1.

TABLE 1

| Example No. | Step 1*[1] | | | Step 2*[2] | | | β-isomer/ α-isomer | Yield (%) |
|---|---|---|---|---|---|---|---|---|
| | Secondary Amine | Temp. (°C.) | Time (hour) | Solvent | Temp. (°C.) | Time (hour) | | |
| 5 | i-Bu$_2$NH | 0 | 0.5 | CH$_2$Cl$_2$ | 15 | 0.5 | 69/31 | 55 |
| 6 | i-Pr$_2$NH | 0 | 0.5 | DME*[3] | 15 | 0.5 | 78/22 | 55 |
| 7 | i-Pr$_2$NH | 0 | 0.5 | AcOEt | 15 | 0.5 | 92/8 | 59 |
| 8 | Et$_2$NH | 0 | 0.5 | MeCN | 15 | 0.5 | 77/23 | 42 |
| 9 | Et$_2$NH | 0 | 0.5 | 1,2-DCE*[4] | 15 | 0.5 | 95/5 | 33 |
| 10 | Et$_2$NH | 0 | 0.5 | Toluene | 15 | 0.5 | 88/12 | 56 |

*[1]: The step of adding tert-butylmagnesium chloride to a solution of secondary amine in tetrahydrofuran and stirring.
*[2]: The step of adding a solvent to the prepared enolate compound and dropwise adding an acetoxyazetidinone solution.
*[3]: dimethoxyethane
*[4]: 1,2-dichloroethane

EXAMPLE 11

To a solution of diisopropylamine (1.96 ml, 14 mmol) in tetrahydrofuran (10 ml) which had been cooled to 0° C., a 1.6M butyl lithium solution (7.5 ml) was added dropwise and stirred for 30 min. To this mixture, a solution of (2S)-2-methoxycyclohexanone (1.41 g, 11 mmol) in tetrahydrofuran (10 ml) was added dropwise at 0° C. and stirred for 30 min., and subsequently, magnesium bromide (2.21 g, 12 mmol) was added and stirred for a further 30 min. After the reaction mixture was concentrated under a reduced pressure, the residue was dissolved in tetrahydrofuran (15 ml) and cooled to 0° C., and then a solution of (3R,4R)-4-acetoxy-3-|(R)-1-hydroxyethyl|azetidin-2-one (2.87 g, 10 mmol) in tetrahydrofuran (15 ml) was added dropwise and stirred for 1 hour. To the resultant mixture, methanol (10 ml) and 2N-hydrochloric acid (10 ml) were added for fractionation. The organic phase was washed with a saturated sodium hydrogencarbonate solution (10 ml) and water (10 ml), and concentrated under a reduced pressure to obtain a crude product of (3S,4R)-3-[(R)-1-((tert-butyldimethylsilyl)oxy) ethyl]-4-[(1R,3S)-3-methoxy-2-oxocyclohexyl]azetidin-2-one. The crude product contained 710 mg of the objective β-isomer (IV). The yield was 20%, and the β:α ratio was 72:28.

COMPARATIVE EXAMPLE

Synthesis of (3S,4R)-3-[(R)-1-((tert-butyldimethylsilyl)oxy)ethyl]-4-[(1R,3S)-3-methoxy-2-oxocyclohexyl]azetidin-2-one using 1-Trimethylsilyloxy-6-(S)-methoxy-1-cyclohexene To a solution of 1-trimethylsilyloxy-6-(S)-methoxy-1-cyclohexene (800 mg, 4 mmol) in tetrahydrofuran (5 ml), a tetrahydrofuran solution containing 1 mol/liter of ethylmagnesium bromide was added and stirred at room temperature for 3 days. This mixture was then cooled to 0° C., and a solution of (3R,4R)-4-acetoxy-3-[(1R)-1-tert-butyldimethylsilyloxyethyl)-2-azetidinone (861 mg, 3 mmol) in tetrahydrofuran (5 ml) was added dropwise to the mixture and stirred at 0° C. for 1 hour. The resultant mixture was subjected to addition of 2N hydrochloric acid and extraction with butyl acetate. The organic phase was washed with a saturated sodium hydrogencarbonate solution and water, and concentrated under a reduced pressure to obtain a crude product of (3S,4R)-3-[(R)-1-((tert-butyldimethylsilyl)oxy)ethyl]-4-[(1R,3S)-3-methoxy-2-oxocyclohexyl]azetidin-2-one. The crude product contained 170 mg of the objective β-isomer. The yield was 16%, and the β:α ratio was 90:10.

What is claimed is:

1. A process for producing a cyclohexylazetidinone derivative of the following formula (IV)

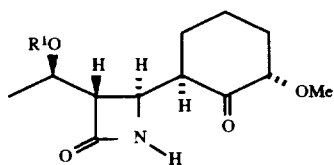

(IV)

in which Me is methyl group, R$^1$ is a hydroxyl-protecting group, wherein said process comprises,
reacting (3R,4R)-4-acyloxy-3-[(1R)-1-hydroxyethyl]-azetidin-2-one derivative of the following formula (III)

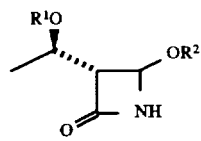

(III)

in which R$^1$ is the same group as described above and R$^2$ is an alkanoyl group having 1 to 9 carbon atoms, a cycloalkanoyl group having 4 to 7 carbon atoms or a benzoyl group, with a magnesium enolate compound of the following formula (II)

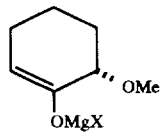

(II)

in which Me is a methyl group and X is a halogen atom.

2. The process claimed in claim 1, wherein said magnesium enolate is obtained by reacting (2S)-2-methoxycyclohexanone of the following formula (I)

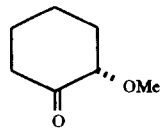

(I)

where Me is a methyl group; with a magnesium amide having the formula (V):

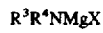

(V)

which is prepared from a secondary amine of the formula (VII),

(VII)

wherein each of R$^3$ and R$^4$ is a lower alkyl group, a lower alkenyl group, a substituted or non-substituted aralkyl group, or a substituted or non-substituted phenyl group, and R$^3$ and R$^4$ may be identical or different, by reacting with a Grignard reagent of the formula (VIII),

(VIII)

wherein R$^5$ is a lower alkyl group, a lower alkenyl group, a substituted or non-substituted aralkyl group, or a substituted or non-substituted phenyl group, and X is a halogen atom.

3. The process according to claim 2, wherein said secondary amine is either diethylamine or diisopropylamine.

4. The process according to claim 1, wherein said magnesium enolate compound is obtained by reacting a corresponding 2-halogeno-cyclohexanone derivative with metallic magnesium.

5. The process according to claim 1, wherein said magnesium enolate compound is obtained by reacting a corresponding lithium enolate derivative with magnesium halide.

6. The process according to claim 1, wherein said magnesium enolate compound is obtained by reacting a corresponding O-trialkylsilyl enol ether derivative with an alkyl magnesium halide.

* * * * *